(12) United States Patent
Breitscheidel et al.

(10) Patent No.: US 6,407,294 B1
(45) Date of Patent: Jun. 18, 2002

(54) METHOD FOR PRODUCING 1,6-HEXANEDIOL

(75) Inventors: Boris Breitscheidel, Limburgerhof; Rolf Pinkos; Frank Stein, both of Bad Dürkheim; Shelue Liang, Ludwigshafen; Rolf Hartmuth Fischer, Heidelberg, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/529,789

(22) PCT Filed: Dec. 10, 1998

(86) PCT No.: PCT/EP98/08072

§ 371 (c)(1),
(2), (4) Date: Apr. 20, 2000

(87) PCT Pub. No.: WO99/33773

PCT Pub. Date: Jul. 8, 1999

(30) Foreign Application Priority Data

Dec. 23, 1997 (DE) .......................... 197 57 554

(51) Int. Cl.$^7$ .................. C07C 27/00; C07C 35/08; C07C 31/13
(52) U.S. Cl. ............... 568/864; 568/822; 568/830; 568/831
(58) Field of Search ................ 568/864, 831, 568/830, 822

(56) References Cited

U.S. PATENT DOCUMENTS

| | | | | |
|---|---|---|---|---|
| 3,933,930 A | | 1/1976 | Dougherty et al. | 260/635 |
| 5,395,990 A | | 3/1995 | Scarlett | 568/864 |
| 5,403,962 A | | 4/1995 | Schneider et al. | 568/885 |
| 5,406,004 A | * | 4/1995 | Eastland et al. | 568/831 |

FOREIGN PATENT DOCUMENTS

| | | |
|---|---|---|
| CA | 2248004 | 8/1998 |
| DE | 196 07 954 A1 | 9/1997 |
| EP | 0552 463 B1 | 7/1993 |
| WO | WO/9731882 | 9/1997 |

* cited by examiner

*Primary Examiner*—Samuel Barts
*Assistant Examiner*—Elvis O. Price
(74) *Attorney, Agent, or Firm*—Keil & Weinkauf

(57) ABSTRACT

A process for producing 1,6-hexanediol by hydrogenation of adipic esters and/or 6-hydroxycaproic esters in the gas phase at elevated temperature and elevated pressure in the presence of chromium-free catalysts comprises hydrogenating a) over a catalyst comprising copper, manganese and aluminum as essential constituents or over Raney copper, b) at a temperature of from 150 to 230° C. and a pressure of from 10 to 70 bar, c) at a molar ratio of hydrogen to ester to be hydrogenated within the range from 150:1 to 300:1, and d) at a catalyst space velocity of from 0.01 to 0.3 kg of $C_6$ ester per liter of catalyst per hour.

12 Claims, 1 Drawing Sheet

METHOD FOR PRODUCING 1,6-HEXANEDIOL

Figure 1:
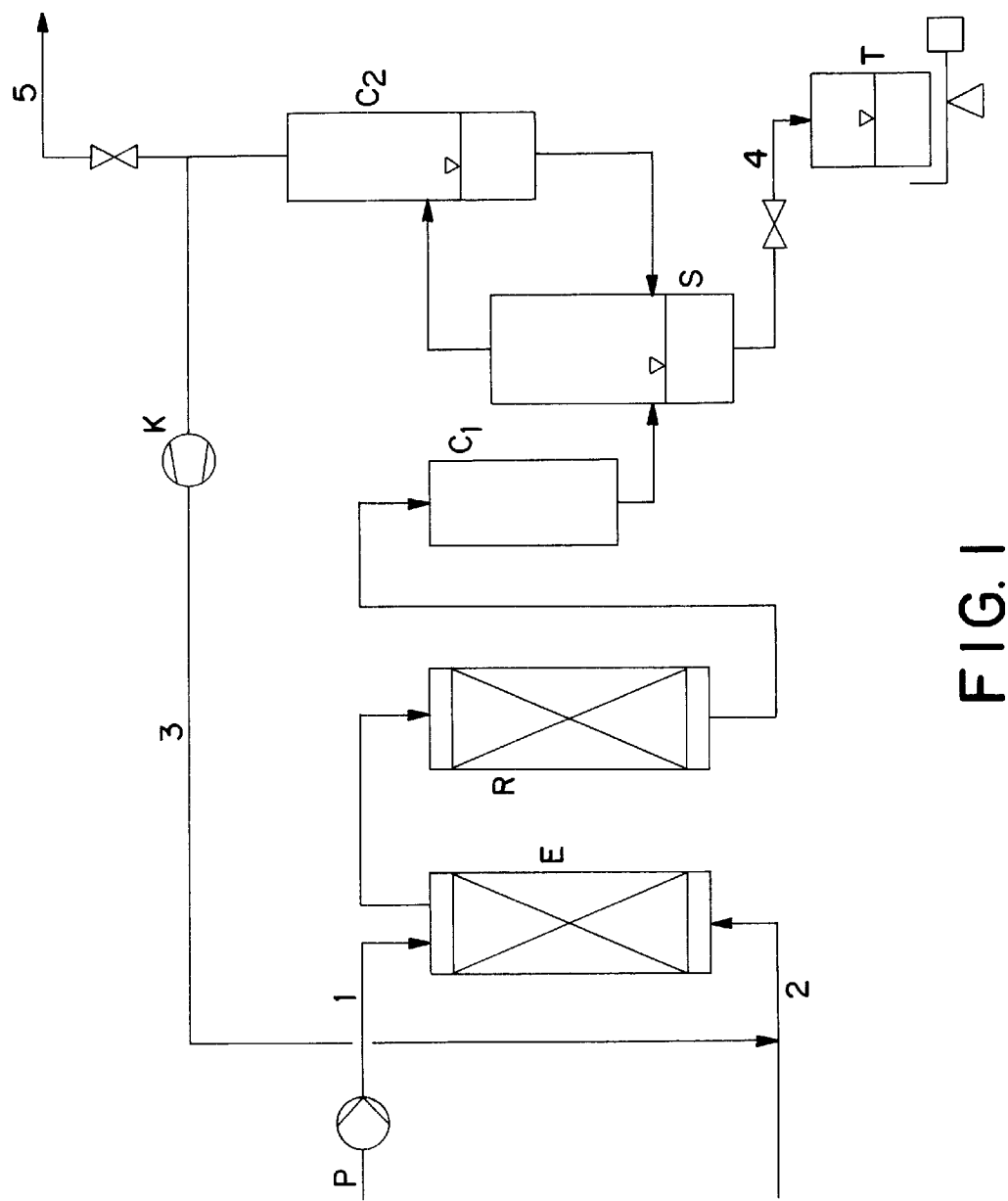

This is the National Phase Application of PCT/EP98/08072, filed Dec. 10, 1998.

The present invention relates to an improved process for producing 1,6-hexanediol by gas phase hydrogenation of adipic diesters, 6-hydroxycaproic esters or mixtures thereof in the presence of chromium-free catalysts comprising essentially copper, manganese and aluminum or in the presence of Raney copper while maintaining certain hydrogenation conditions.

Example 1 of WO 97/31882 discloses hydrogenating mixtures of dimethyl adipate and methyl 6-hydroxycaproate in the liquid phase at 220° C./220 bar in the presence of catalysts comprising 70% by weight of CuO, 25% by weight of ZnO and 5% by weight of $Al_2O_3$ to hexanediol with selectivities of above 99% (conversion 99.5%). The disadvantage of this hydrogenation in the liquid phase is the high reaction pressure, which entails considerable capital costs for the hydrogenation plant. This disadvantage can be eliminated by hydrogenating in the gas phase, since it is generally the case that distinctly lower reaction pressures, for example pressures below 100 bar, are sufficient for ester hydrogenations. However, for such gas phase hydrogenations to be economical, the advantage of the capital cost side must not be lost through other cost factors. A gas phase hydrogenation must therefore achieve a similar, high hexanediol selectivity to the liquid phase hydrogenation.

Japanese Laid-Open Application S 64-85938 discloses hydrogenating dimethyl adipate or diethyl adipate to hexanediol in the gas phase in the presence of copper chromite catalysts at 160–250° C. and 10 to 70 atmospheres and diester/hydrogen molar ratios of 1:100 to 1:590. A hexanediol selectivity of above 98% is achieved in only one of eleven operative examples, viz., a hexanediol selectivity of 98.9% (conversion 97.5%) in Example 6. However, the employed hydrogen/diester molar ratio of 457 leads to very high energy costs. Finally, chromium-containing catalysts are undesirable because of the toxicity of chromium. Safe landfilling of deactivated catalysts is very costly.

U.S. Pat. No. 5,395,990 states for the dimethyl adipate gas phase hydrogenation of Example 13, which is carried out at 180° C. and 62 bar over a catalyst comprising copper (41.1% by weight), manganese (6.2% by weight) and aluminum (20.4% by weight) with a hydrogen/diester molar ratio of 480 and a catalyst space velocity of 0.4 l of diester per l of catalyst per hour, that the results obtained are similar to those of Example 11. However, Example 11, a gas phase hydrogenation of dimethyl maleate under identical conditions to Example 13, does not report the butanediol selectivity.

Example 13 of U.S. Pat. No. 5,406,004 discloses hydrogenating dimethyl adipate to hexanediol at 220° C. and 62 bar, a diester/hydrogen molar ratio between 248 and 383 and a catalyst space velocity of 0.4 l of diester per l of catalyst per hour in the presence of the catalyst mentioned in Example 13 of U.S. Pat. No. 5,395,990. Hexanediol selectivity and diester conversion are not reported. It is merely stated that similar results are observed to Examples 2 to 4. However, these examples do not amount to a true gas phase hydrogenation, since the temperature of the reactor exit mixture is below its dew point.

We have repeated Example 13 of U.S. Pat. No. 5,395,990 and Example 13 of U.S. Pat. No. 5,406,004 (as Comparative Examples 14 and 15) and found that the hexanediol selectivity is in each case distinctly below 95%. There are two groups of by-products in particular which are responsible for the low hexanediol selectivity:

a) 5-membered Ring Compounds:

2-methylcyclopentanol (1), 2-methylcyclopentanone (2), cyclopentanol (3) and hydroxymethylcyclopentane (4), which can all be formed from dimethyl adipate:

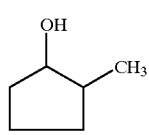
(1)

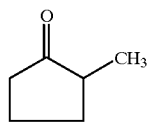
(2)

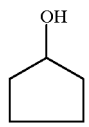
(3)

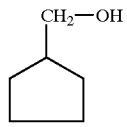
(4)

The methanol released in the course of the gas phase hydrogenation of dimethyl adipate could be acting as a methylating agent.

By way of example, the 5-membered ring compounds are obtained in the proportions of 61% of (1), 29% of (2), 6% of (3) and 4% of (4), based on total 5-membered ring compounds, in Example 5.

The process described in EP-A 251 111, which comprises reacting adipic diesters at 300 to 345° C. in the gas phase over solid oxidic catalysts of elements of main group I to V and of transition groups I to VIII of the Periodic Table of the Elements or oxides of the rare earth metals, especially aluminum oxide, even promotes cyclopentanone to the main product.

b) $C_{12}$ and $C_{13}$ Esters

The transesterification of methyl 6-hydroxycaproate with hexanediol gives rise to 6-hydroxyhexyl 6-hydroxycaproate (5).

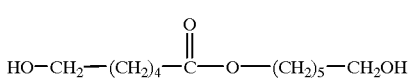
(5)

Another product, albeit in a much smaller quantity than (5), is 6-hydroxyhexyl methyl adipate (6), formed presumably through transesterification of dimethyl adipate with hexanediol.

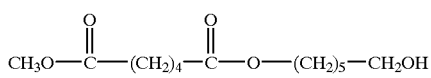

(6)

The molar ratio of (5) to (6) is about 90:10.

The quantitatively dominant by-product (5) has a significantly higher molecular weight (MW 232) and hence a distinctly higher boiling point than dimethyl adipate (MW 174) and methyl 6-hydroxycaproate (MW 146).

The greater the production of (5) and (6), the higher the temperatures and/or hydrogen rates required to vaporize and gas-phase hydrogenate (5) and (6). And removing (5) and (6) from the hydrogenation reactor exit stream, for recycling, is complicated. Therefore, unless they can be hydrogenated, they must both be considered by-products.

It is an object of the present invention to provide a process for gas phase hydrogenation of adipic diesters, 6-hydroxycaproic esters or mixtures of adipic diesters and 6-hydroxycaproic esters to hexanediol in the presence of predominantly copper catalysts with hexanediol selectivities of not less than 95%, especially more than 98%, coupled with $C_6$ ester conversions of not less than 90%, especially not less than 95%.

We have found that this object is achieved according to the present invention by a process for producing hexanediol by hydrogenation of adipic esters and/or 6-hydroxycaproic esters at elevated temperature and elevated pressure in the presence of chromium-free catalysts, which comprises hydrogenating a) over a catalyst comprising copper, manganese and aluminum as essential constituents or over Raney copper, b) at a temperature of from 150 to 230° C. and a pressure of from 10 to 70 bar, c) at a molar ratio of hydrogen to ester to be hydrogenated within the range from 150:1 to 300:1, and d) at a catalyst space velocity of from 0.01 to 0.3 kg of $C_6$ ester per liter of catalyst per hour.

It is surprising that it is possible to keep the sum total of by-produced 5-membered ring compounds and 6-hydroxyhexyl esters of $C_6$ acid at below 5 mol %, especially 2 mol % (based on feed of adipic diester and 6-hydroxycaproic ester) and so achieve a hexanediol selectivity of not less than 95%, especially not less than 98%:

The gas phase hydrogenation of dimethyl adipate and methyl 6-hydroxycaproate, as mentioned earlier, by-produces (presumably via methyl cyclopentanone-2-carboxylate and cyclopentanone) 2-methylcyclopentanol, 2-methylcyclopentanone, cyclopentanol and hydroxymethylcyclopentane. These by-products are typical of the hydrogenation of esters of $C_6$ monocarboxylic and dicarboxylic acids. They are therefore not observed in the hydrogenation of alpha, omega-diesters of $C_4$, $C_5$, $C_7$ and $C_8$ acids. And their amount increases with increasing temperature.

The gas phase hydrogenation of adipic diesters also by-produces the high boiling 6-hydroxyhexyl 6-hydroxycaproate and 6-hydroxyhexyl methyl adipate esters. They are increasingly hydrogenated to hexanediol, the product of value, with increasing temperature.

Despite the mutually contrary response of the two groups of by-products to changes in the temperature, it is surprisingly possible to attain the desired selectivity of 95% or 98%.

Nor was it foreseeable that, by-product formation notwithstanding, the catalyst would have a long effective life.

Furthermore, both high hexanediol selectivities and long catalyst lives are surprisingly obtained on using adipic diester/6-hydroxycaproic ester mixtures produced according to DE-A 19 607 954, which include numerous other compounds.

The starting materials for the process of the present invention can be pure adipic esters, for example $C_1$–$C_4$-dialkyl diesters, 6-hydroxycaproic esters, for example $C_1$–$C_4$-alkyl esters, or mixtures thereof. It is preferably possible to use ester mixtures as obtained in the esterification with $C_1$–$C_4$ alcohols of carboxylic acid mixtures by-produced in the oxidation of cyclohexane to cyclohexanone/cyclohexanol. These mixtures may further include, for example, glutaric diesters, 5-hydroxyvaleric esters, 2-oxocaproic esters and dihydromuconic diesters.

The process of the present invention is preferably operated using methyl and ethyl esters of the abovementioned carboxylic acids as starting materials.

The hydrogenation is effected catalytically in the gas phase.

Suitable catalysts are chromium-free catalysts comprising essentially copper, manganese and aluminum with or without minor amounts of zinc, zirconium and/or silicon.

This includes in particular catalysts as described in EP 0 552 463. These are catalysts which, in the oxidic form, have the composition

where a>0, b>0, c≧0, d>0, a>b/2, b>a/4, a>c, a>d and x is the number of oxygen ions required per unit formula to preserve electrical neutrality. A specific example of a suitable catalyst is composed of about 70% by weight of CuO, 20% by weight of $Al_2O_3$ and 10% by weight of $Mn_2O_3$.

The catalysts can be prepared, for example according to EP 0 552 463, by precipitation of sparingly soluble compounds from solutions comprising the corresponding metal ions in the form of their salts. Examples of suitable salts are halides, sulfates and nitrates. Suitable precipitants include all agents leading to the formation of such insoluble intermediates as are convertible into the oxides by thermal treatment. Particularly suitable intermediates are the hydroxides and carbonates or bicarbonates, so that the precipitants used are particularly preferably alkali metal carbonates or ammonium carbonates. An important step in the preparation of the catalysts is the thermal treatment of the intermediates at temperatures between 500° C. and 1000° C. The BET surface area of the catalysts is within the range from 10 to 150 $m^2/g$.

Alternatively, Raney copper can be used as catalyst; Raney copper is conventionally preparable by treating copper-aluminum alloys with alkali metal hydroxides and used in piece form.

The catalysts can be disposed in a fixed bed reactor or in a fluidized bed reactor. The hydrogenation can be carried out in downflow or upflow mode. It is advantageous to use at least sufficient hydrogen as hydrogenant and carrier gas to prevent starting materials, intermediates and products from ever liquefying during the reaction. The excess hydrogen is preferably recycled, although a small portion may be removed from the system as exhaust gas in order that inerts, for example methane, may be removed. It is possible to use one reactor or a plurality of reactors connected in series or in parallel.

The hydrogenation temperature is within the range from 150° C. to 230° C., preferably within the range from 160° C. to 200° C., particularly preferably within the range from 170° C. to 190° C.

The reaction pressure is within the range from 10 bar to 70 bar, preferably within the range from 20 bar to 60 bar, particularly preferably within the range from 30 bar to 50 bar.

The molar ratio of hydrogen to the sum total of the $C_6$ esters used is within the range from 150 to 300, preferably within the range from 170 to 290, particularly preferably within the range from 180 to 280.

The catalyst space velocity is within the range from 0.01 to 0.3, preferably within the range from 0.05 to 0.2, particularly preferably within the range from 0.05 to 0.15, kg of $C_6$ ester to be hydrogenated per 1 of catalyst per hour.

The conversion, based on the sum total of hexanediol-forming $C_6$ compounds such as adipic diesters, 6-hydroxycaproic esters, caprolactone and dihydromuconic diesters, shall be more than 90%, especially more than 95%.

The hydrogenation is advantageously carried out as a continuous process. The hydrogenation exit streams are condensed and preferably worked up by distillation.

The hydrogenation exit stream consists essentially of 1,6-hexanediol and the alcohol corresponding to the ester group. Further constituents, in particular on using ester mixtures produced according to DE-A 19607954, are 1,5-pentanediol, 1,4-butanediol, 1,2-cyclohexanediols and also monoalcohols having from 1 to 6 carbon atoms and water.

Unconverted starting compounds present in the hydrogenation exit stream can be removed by distillation and recycled into the hydrogenation stage.

BRIEF DISCRIPTION OF THE DRAWING

FIG. 1 depicts a schematic drawing of a hydrogenation apparatus.

EXAMPLES

A) Hydrogenation Apparatus:

Continuous runs were carried out in the hydrogenation apparatus schematically depicted in FIG. 1. It consists of a vaporizer (E), a 1.4 l tubular reactor (30×2000 mm) (R), two condensers $C_1$ and $C_2$ and a pressure separator (S) to recover condensable components from the hydrogen stream, a cycle gas compressor (K) for recycling the cycle gas hydrogen (3) and a discharge vessel (T) for collecting the reaction effluent (4).

Procedure:

Examples 1–12 and Examples 14 and 15 were each carried out using a CuO (70% by weight)/$Mn_2O_3$ (10% by weight)/$Al_2O_3$ (20% by weight) catalyst from Sudchemie (T4489), which was activated in the reactor at 160–200° C. using hydrogen/nitrogen mixtures in a volume ratio of from 1:99 to 100:0. The catalyst zone was bounded by a layer of quartz rings at the upstream end and the downstream end. Cycle gas was employed in all cases, although 10% of the cycle gas (5) was bled from the system and replaced by the same amount of fresh hydrogen.

Example 13 was carried out using the Raney copper catalyst A 3900 from Activated Metals.

The $C_6$ ester starting compounds (1) were metered with a pump (P) into the vaporizer, where they were vaporized and passed in gaseous form and mixed with preheated hydrogen (2) into the reactor. The ester/hydrogen molar ratio was determined by weighing the feed of starting material and measuring the hydrogen streams.

The hydrogenation exit stream was weighed after condensing. Its composition was determined quantitatively by gas chromatography using an internal standard (diethylene glycol dimethyl ether). Each run was operated for about four days without change before the hydrogenation exit stream was analyzed.

Inventive Examples 1–12

These Examples were carried out using 500 ml of CuO/$Mn_2O_3$/$Al_2O_3$ catalyst. Pure dimethyl adipate (density d=1.063 according to page 36 of the catalog of Aldrich-Chemie, 1994, Steinheim) was used.

In Example 12, the dimethyl adipate was replaced by a mixture, produced according to DE-A 19 607 954, of dimethyl adipate, methyl 6-hydroxycaproate and further esters. The composition of the mixture was 52.3% of dimethyl adipate, 9.1% of methyl 6-hydroxycaproate, 5.2% of caprolactone, 4.1% of dimethyl dihydromuconate, 1.5% of dimethyl succinate, 2.5% of valerolactone, 2.2% of 5-hydroxyvaleric ester, 2.7% of 2-oxocaproic ester and 6.4% of dimethyl glutarate (by weight in each case).

Inventive Example 13

Pure dimethyl adipate was used. 500 ml of Raney copper were used as catalyst.

Comparative Examples 14–16

Comparative Example 14 was a repeat of Example 13 of U.S. Pat. No. 5,395,990 and Comparative Example 15 was a repeat of Example 13 of U.S. Pat. No. 5,406,004: 220° C.; molar ratio of dimethyl adipate/hydrogen=1:248. 150 ml of CuO/$Mn_2O_3$/$Al_2O_3$ catalyst were used.

All the results are shown below in Table 1.

Hydrogenation of dimethyl adipate in the gas phase over catalyst T 4489

| Examples | Temp. [° C.] | Pressure [bar] | Ester/$H_2$ (molar ratio) | Space velocity [kg/1*h] | Conversion [mol %] | Selectivity [mol %] | | |
|---|---|---|---|---|---|---|---|---|
| | | | | | | HDO | 5-membered ring compounds[1] | $C_{12} + C_{13}$ ester[2] |
| 1 | 170 | | | | 100 | 96.6 | 0.3 | 1.2 (2.4)[3] |
| 2 | 180 | | | | 100 | 98.1 | 0.4 | 0.7 (1.4) |
| 3 | 190 | 45 | 1:280 | 0.1 | 100 | 96.8 | 1.3 | 0.5 (1.0) |
| 4 | 200 | | | | 100 | 95.5 | 3.5 | 0.4 (0.8) |
| 5 | 210 | | | | 100 | 89.7 | 6.8 | 0.2 (0.4) |
| 6 | | 35 | | | 99.7 | 96.3 | 1.3 | 0.7 (1.4) |
| 7 | 190 | 25 | 1:280 | 0.1 | 99.4 | 95.3 | 1.5 | 0.9 (1.8) |
| 8 | | 15 | | | 97.4 | 95.0 | 1.7 | 1.2 (2.4) |
| 9 (Comp.) | 190 | 25 | 1:100 | 0.1 | 99.8 | 69.4 | 1.2 | 9.3 (18.6) |
| 10 (Comp.) | | | 1:140 | 0.2 | 100 | 80.1 | 1.1 | 5.4 (10.8) |
| 11 (Comp.) | 190 | 45 | 1:80 | | 100 | 67.4 | 1.1 | 7.4 (14.8) |

-continued

Hydrogenation of dimethyl adipate in the gas phase over catalyst T 4489

| Examples | Temp. [° C.] | Pressure [bar] | Ester/H$_2$ (molar ratio) | Space velocity [kg/1*h] | Conversion [mol %] | Selectivity [mol %] | | |
|---|---|---|---|---|---|---|---|---|
| | | | | | | HDO | 5-membered ring compounds[1] | C$_{12}$ + C$_{13}$ ester[2] |
| 12[4] | 190 | 45 | 1:280 | 0.1 | 99.5 | 96.7 | 1.5 | 0.2 (0.4) |
| 13[5] | 220 | 45 | 1:280 | 0.1 | 97.7 | 95.0 | 1.5 | 0.4 (0.8) |
| 14 (Comp.) | 180 | 60 | 1:520 | 0.4 | 91.7 | 85.2 | 0.3 | 3.3 (6.6) |
| 15 (Comp.) | 220 | 60 | 1:250 | 0.4 | 99.3 | 88.5 | 6.7 | 0.3 (0.6) |

[1] 2-methylcyclopentanol + 2-methylcyclopentanone + cyclopentanol + hydroxymethlcyclopentane
[2] 6-hydroxyhexyl 6-hydroxycaproate + 6-hydroxyhexyl methyl adipate
[3] the hydrogenation of one mole of C$_{12}$ or C$_{13}$ ester produces two moles of hexanediol
[4] use of dimethyl adipate/methyl 6-hydroxycaproate mixtures instead of pure dimethyl adipate
[5] use of Raney copper instead of T 4489

We claim:

1. A process for producing 1,6-hexanediol by hydrogenation of adipic esters and/or 6-hydroxycaproic esters in the gas phase at elevated temperature and elevated pressure in the presence of chromium-free catalysts, which comprises hydrogenating in a hydrogenation reactor
   a) over a catalyst comprising copper, manganese and aluminum as essential constituents or over a Raney copper,
   b) in the gas phase such that the reactants, intermediates and products are maintained in the gas phase in said reactor, at a temperature from 160 to 200° C. and a pressure of from 10 to 70 bar,
   c) at a molar ratio of hydrogen to ester to be hydrogenated within the range from 150:1 to 300:1, and
   d) at a catalyst space velocity of from 0.01 to 0.3 kg of C$_6$ ester per liter of catalyst per hour.

2. A process as claimed in claim 1, wherein the catalyst further comprises zinc, zirconium and/or silicon.

3. A process as claimed in claim 1, wherein the catalyst space velocity used ranges from 0.05 to 0.2 kg of C$_6$ ester per liter of catalyst per hour.

4. A process as claimed in claim 1, wherein the catalyst space velocity used ranges from 0.05 to 0.15 kg of C$_6$ ester per liter of catalyst per hour.

5. A process as claimed in claim 1, wherein the molar ratio of hydrogen to C$_6$ ester is within the range from 170 to 290.

6. A process as claimed in claim 1, wherein the molar ratio of hydrogen to C$_6$ ester is within the range from 180 to 280.

7. A process as claimed in claim 1, wherein the temperature is within the range from 170 to 190° C.

8. A process as claimed in claim 1, wherein the pressure is within the range from 20 to 60 bar.

9. A process as claimed in claim 1, wherein the pressure is within the range from 30 to 50 bar.

10. A process as claimed in claim 1, wherein the ester to be hydrogenated comprises a mixture of adipic diester and 6-hydroxycaproic ester.

11. A process as claimed in claim 1, wherein the starting materials used are C$_1$–C$_4$-alkyl monoesters of 6-hydroxycaproic acid and/or C$_1$–C$_4$-alkyl diesters of adipic acid.

12. A process as claimed in claim 1, wherein the starting materials to be hydrogenated are ester mixtures as generated by esterification of carboxylic acid mixtures obtained as by-products in the production of cyclohexanol/cyclohexanone by oxidation of cyclohexane with oxygen-comprising gases.

* * * * *